United States Patent
Krishnamachari

(12) United States Patent (10) Patent No.: US 8,488,118 B2
Krishnamachari (45) Date of Patent: Jul. 16, 2013

(54) APPARATUS AND METHOD FOR MULTI-MODAL IMAGING IN NONLINEAR RAMAN MICROSCOPY

(75) Inventor: Vishnu Vardhan Krishnamachari, Mannheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 162 days.

(21) Appl. No.: 13/048,353

(22) Filed: Mar. 15, 2011

(65) Prior Publication Data

US 2011/0222054 A1 Sep. 15, 2011

(30) Foreign Application Priority Data

May 15, 2010 (DE) .................. 10 2010 015 964

(51) Int. Cl.
*G01J 3/44* (2006.01)
(52) U.S. Cl.
USPC ........................................ 356/301
(58) Field of Classification Search
USPC ............................. 356/301, 72–73
See application file for complete search history.

(56) References Cited

U.S. PATENT DOCUMENTS

| 2004/0057047 | A1 | 3/2004 | Knebel |
| 2006/0238745 | A1 | 10/2006 | Hashimoto et al. |
| 2007/0272838 | A1 | 11/2007 | Kudo et al. |
| 2008/0059135 | A1 | 3/2008 | Murugkar et al. |
| 2008/0151235 | A1* | 6/2008 | Oshima et al. ............ 356/237.4 |
| 2008/0192260 | A1 | 8/2008 | Seong et al. |
| 2008/0304047 | A1* | 12/2008 | Lee et al. ..................... 356/51 |
| 2009/0114859 | A1 | 5/2009 | Prasad et al. |

FOREIGN PATENT DOCUMENTS

| DE | 102005044422 A1 | 3/2007 |
| DE | 102008059579 A1 | 7/2010 |
| EP | 2157415 A1 | 2/2010 |

* cited by examiner

*Primary Examiner* — Tarifur Chowdhury
*Assistant Examiner* — Abdullahi Nur
(74) *Attorney, Agent, or Firm* — Patentbar International P.C.

(57) ABSTRACT

An apparatus for the microscopic examination of an object has an illumination system which generates a first illumination light beam and a second illumination light beam. A first polarization filter (28) circularly polarizes the first illumination light beam. A second polarization filter (32) linearly polarizes the second illumination light beam. A modulator (34) allows a modulation of the polarized second illumination light beam. An excitation optical system directs the two illumination light beams onto an object. A detection optical system directs detection light beams emanating from the object onto at least two detector units, a first detector unit detecting a first nonlinear Raman effect and a second detector unit detecting a second nonlinear Raman effect.

14 Claims, 2 Drawing Sheets

APPARATUS AND METHOD FOR MULTI-MODAL IMAGING IN NONLINEAR RAMAN MICROSCOPY

CROSS-REFERENCE TO RELATED APPLICATIONS

This Application claims priority to German Patent Application No. DE 10 2010 015 964.6 filed on Mar. 15, 2010, that is incorporated herein by reference in its entirety.

FIELD OF THE INVENTION

The invention relates to an apparatus for the microscopic examination of an object. The apparatus has an illumination system and a first polarization filter. The illumination system generates a first illumination light beam and a second illumination light beam. The first polarization filter circularly polarizes the first illumination light beam.F

BACKGROUND OF THE INVENTION

Various Raman techniques are known to examine biological and biochemical samples. Linear Raman microscopy consists of irradiating a sample with a strong laser beam and detecting the frequency-modulated detection light emanating from the sample. This technique is, however, too slow to detect processes in the biological and biochemical samples in real-time in a sufficiently precise manner.

In addition, nonlinear Raman techniques are known to solve the problem of the too slow imaging. Among these nonlinear Raman techniques is the observation of coherent anti-Stokes and Stokes scattering (CARS, CSRS). Here, the sample is irradiated collinearly with radiation with two distinct frequencies. As soon as the difference between the two frequencies matches a vibrational resonance frequency in the sample, the sample emits strong Stokes and anti-Stokes radiation which can be detected individually or simultaneously.

A further nonlinear Raman technique which is used for examination under a microscope is stimulated Raman scattering (SRS), in particular 'Stimulated Raman Gain' (SRG) or 'Stimulated Raman Loss' (SRL). Similar to coherent Stokes or anti-Stokes scattering, the sample is irradiated with radiation with two distinct frequencies. If the sample has a resonance frequency that matches the difference between the two exciting frequencies, energy is transferred from the radiation with higher frequency to the radiation with lower frequency. This change in energy is observed and allows conclusions on the structures and processes in the sample. Here, the observation of the increase in energy for the lower frequency is referred to as SRG and the observation of the respective decrease in energy for the higher frequency is referred to as SRL.

One problem with these techniques is that the exciting radiation and the detection radiation have the same wavelength and polarization. Thus, for the detection signal there results a very strong background signal that makes the detection of the sought-for signal more difficult. One possibility of suppressing the background in the case of SRS is the modulation of the exciting radiation. Another disadvantage of CARS or CSRS is that the image obtained from the detection radiation contains chemically non-specific information as images obtained with CARS or CSRS also comprise non-resonant signals.

A Raman technique which has the advantages but not the disadvantages of the afore-mentioned techniques is the observation of the Raman-induced Kerr effect (RIKES). Here, the sample is again irradiated with radiation of two distinct frequencies, the radiation of one frequency being circularly polarized and the other one being linearly polarized. The RIKES signal then emitted by the sample is polarized orthogonally to the incident radiation of the same frequency. The RIKES signal is fast and chemically specific, however, compared to the other detection signals it is relatively weak.

SUMMARY OF THE INVENTION

It is the object of the invention to specify a method and an apparatus for the microscopic examination of an object, which enable that fast-running microscopic processes are resolved with high chemical precision and displayed.

This object is solved by the features of the independent claims. Advantageous embodiments are specified in the subclaims.

According to a first aspect, the invention is characterized by a second polarization filter that p-polarizes the second illumination light beam and by a modulator for modulating the polarized second illumination light beam. An excitation optical system directs the two illumination light beams onto an object, in particular a sample. A detection optical system directs the detection light beams emanating from the object onto at least two detector units. A first detector unit detects a first nonlinear Raman effect, and a second detector unit detects a second nonlinear Raman effect.

The detection of two distinct nonlinear Raman effects with one single apparatus enables, on the one hand, to precisely display fast-running microscopic processes and, on the other hand, to resolve the structures involved in these processes with high precision. The first illumination light beam is characterized by its circular polarization, and the second illumination light beam is characterized by its linear polarization and its modulation capability. The light source preferably comprises one or two light-generating single devices, for example one or two laser devices.

In this connection it is particularly advantageous when a third detector unit for detecting a third nonlinear Raman effect is provided. Further, each time, at least two of the three nonlinear Raman effects can be detected simultaneously. In addition, all three nonlinear Raman effects can be detected simultaneously.

In an advantageous embodiment, the first illumination light beam is a pump laser beam and the second illumination light beam is a Stokes laser beam. A first wavelength-selective element directs radiation of a first wavelength range of the detection light beam, in which wavelengths of a Stokes emission or anti-Stokes emission lie, via a third polarization filter that p-polarizes the light of the first wavelength range onto a first detector that is at least sensitive in the first wavelength range. A second wavelength-selective element separates radiation of a second wavelength range of the detection light beam, in which wavelengths of the first illumination light beam lie, from a third wavelength range, in which wavelengths of the second illumination light beam lie, and directs the radiation of the second wavelength range onto a second detector that is sensitive in the second wavelength range. A fourth polarization filter p-polarizes the light of the second wavelength range before it is incident on the second detector. A demodulator demodulates the output signal of the second detector. A fifth polarization filter s-polarizes the light of the third wavelength range directed on the third detector, the third detector being sensitive in the third wavelength range. The demodulator can also be integrated in the second detector. The first to third detectors can also be referred to as detector units.

This enables to detect at least two of the three nonlinear Raman effects with one single device and, in particular, to detect at least two of the three nonlinear Raman effects at the same time. The pump laser beam and the Stokes laser beam are characterized by their wavelengths. In particular, the pump laser beam has wavelengths between 750 and 980 nm and the Stokes laser beam has a wavelength of 1064 nm. Preferably, an SRL signal is detected by the second detector and a RIKES signal is detected by the third detector.

Alternatively, the first illumination light beam is the Stokes laser beam and the second illumination light beam is the pump laser beam. The first wavelength-selective element directs the first wavelength range of the detection light beam via the third polarization filter onto the first detector. The second wavelength-selective element directs radiation of the second wavelength range of the detection light beam onto a fourth detector that is at least sensitive in the second wavelength range. A sixth polarization filter s-polarizes the light of the second wavelength range before it is incident on the fourth detector. A seventh polarization filter p-polarizes the light of the third wavelength range directed onto a fifth detector that is sensitive in the third wavelength range. A demodulator demodulates the output signal of the fifth detector. The demodulator can also be integrated in the fifth detector. Preferably, the RIKES signal is detected by the fourth detector and an SRG signal is detected by the fifth detector.

The precision in the examination of the object can be increased further in that the components are arranged such that the detection beams emitted in forward direction with respect to the illumination light beams and/or the detection beams emitted in reverse direction are detected.

According to a second aspect of the invention, the invention is characterized by a method for examining an object with a microscope and in particular with the apparatus for the microscopic examination of an object. Preferably, the CARS or CSRS signal are detected simultaneously with the RIKES signal.

BRIEF DESCRIPTION OF THE DRAWINGS

In the following, embodiments of the invention are explained in more detail with reference to schematic drawings.

Elements having the same structure or function are identified with the same reference signs throughout all Figures.

DETAILED DESCRIPTION OF THE PREFERRED EMBODIMENTS

Figure 1:
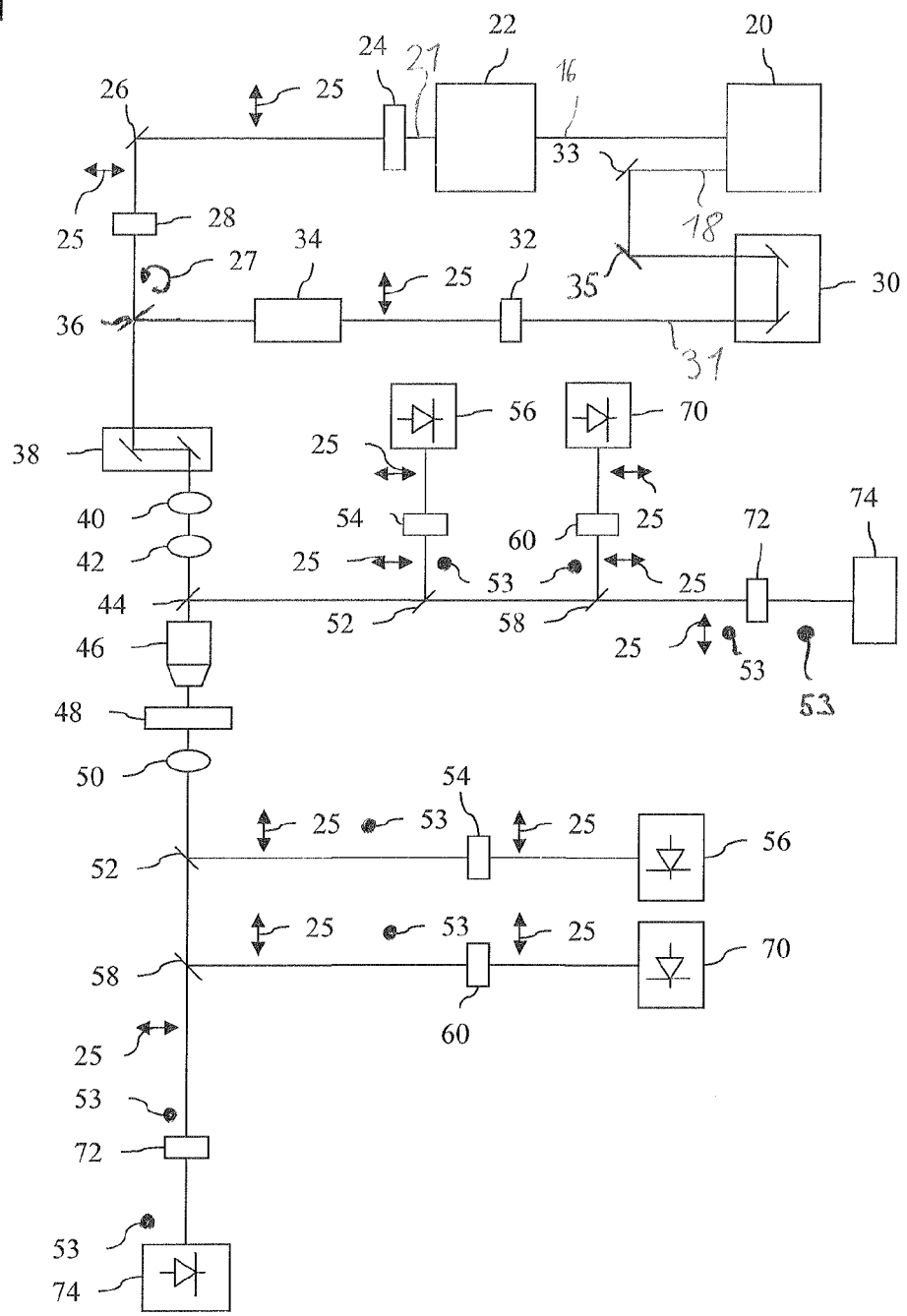
FIG. 1 shows a first embodiment of an apparatus for the microscopic examination of an object.

FIG. 1 shows an apparatus for the microscopic examination of an object, in particular a confocal scanning microscope. The microscope comprises an illumination system. The illumination system comprises a light source 20 generating laser radiation that is internally split into a first laser beam 16 and a second laser beam 18. The light source 20 comprises, for example, an OPO pump laser. The first laser beam 16 preferably has a wavelength of 532 nm, and the second laser beam 18 preferably has a wavelength of 1064 nm. The first laser beam 16 passes through an optical parametric oscillator 22 (OPO) of the illumination system, with the aid of which the wavelength of the first laser beam 16 can be converted into wavelengths between, for example, 750 nm and 980 nm, and a first polarization filter 24 of the illumination system that p-polarizes (illustrated by an arrow 25) the converted first laser beam 16 which is referred to as pump laser beam 21 after passing through the optical parametric oscillator 22. A first mirror 26 directs the p-polarized pump laser beam 21 onto a circular polarization filter 28 of the illumination system that circularly polarizes the pump laser beam 21. The circular polarization filter 28 preferably comprises a rotatable quarter-wave plate. The light source 20 can comprise one or two single laser devices for generating the first and second laser beam 16, 18.

The second laser beam 18 is referred to hereinafter as Stokes laser beam 31 and is directed via a second mirror 33, a third mirror 35 and a delay stage 30 onto a second polarization filter 32 of the illumination system that p-polarizes the Stokes laser beam 31. For modulating the p-polarized Stokes laser beam 31, a modulator 34 of the illumination system is provided, for example an acousto-optic modulator. Via a first dichroic beam splitter 36, the circularly polarized pump laser beam 21 and the p-polarized, possibly modulated Stokes laser beam 31 are combined and directed onto a scanning unit 38. Starting out from the scanning unit 38, the two combined beams 21, 31 pass through a scan lens 40 and a tube lens 42 and are directed onto the sample 48 via a beam splitter 44 and an objective 46.

Detection beams emanating from the sample 48 are directed in forward and reverse direction of the illumination light beams 21, 31 via a condenser 50 and via the beam splitter 44, respectively, onto a first wavelength-selective element 52. The first wavelength-selective element 52 comprises, for example, a dichroic beam splitter (long-pass) and deflects the portion of the detection light beams whose wavelengths lie in the first wavelength range towards a third polarization filter 54 that filters out the p-polarized portion from portions of the two laser beams 21, 31 and allows it to pass to a first detector 56. Wavelengths of a coherent anti-Stokes emission (CARS) lie in the first wavelength range. Light of wavelengths higher than those of CARS is allowed to pass through the first wavelength-selective element 52.

A second wavelength-selective element 58 comprises, for example, a dichroic beam splitter (long-pass) and deflects a portion of the detection light whose wavelengths lie in a second wavelength range towards a fourth polarization filter 60 that allows the p-polarized portion of the two laser beams 21, 31 to pass through to a second detector 70. The second detector 70 comprises, for example, a large-surface photodiode with lock-in-detection for demodulation and detects the SRL signal. The second wavelength-selective element 58 reflects light with wavelengths that correspond to the pump laser radiation and allows light of higher wavelengths to pass through. The first and second wavelength-selective elements 52, 58 allow the other wavelength portions of the detection light, in particular radiation of a third wavelength range, to pass through to a fifth polarization filter 72 that only allows the s-polarized portion of the two laser beams 21, 31 to pass through to a third detector 74. The third detector 74 detects the RIKES signal and preferably comprises a photomultiplier tube that is sensitive in the near infrared. The Stokes laser radiation lies in the third wavelength range.

During operation of the microscope, in a first step for capturing fast processes in the sample 48, the Stokes laser beam 31 is not modulated, and with the aid of the first wavelength-selective element 52 the first wavelength range of the detection light beam, in which wavelengths of the anti-Stokes emission (CARS) emanating from the sample 48 lie, is p-polarized and directed onto the first detector 56. With the aid of the fifth polarization filter 72 radiation of the third wavelength range of the detection light beam is s-polarized and directed onto the third detector 74. Thus, the CARS signal is detected with the first detector 56 and preferably the RIKES signal is simultaneously detected with the third detector 74. In this way, the CARS signal is particularly strong, and the RIKES signal is almost free of non-resonant background radiation.

In a second step, the Stokes laser beam 31 is modulated with the aid of the modulator 34. Radiation of the second wavelength range of the detection light beam is p-polarized and directed onto the second detector 70. An output signal of the second detector 70 is then demodulated with the aid of a demodulator integrated in the second detector 70 for obtaining the measurement signal. Alternatively, the demodulator can also be designed as a separate component part. The demodulated SRL signal is used for a quantitative analysis.

Figure 2:
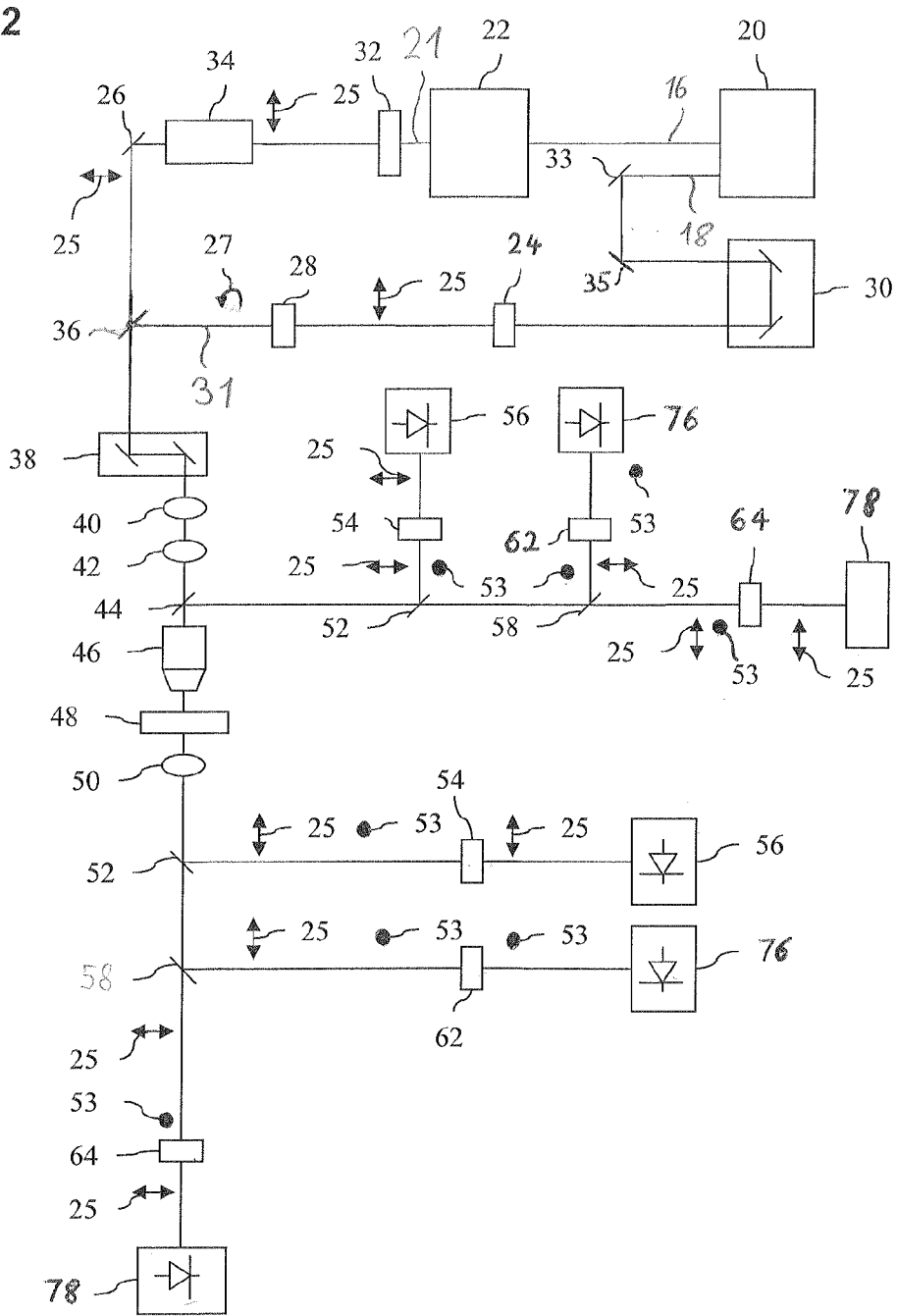
FIG. 2 shows a second embodiment of the apparatus for the microscopic examination of an object.

FIG. 2 shows an alternative embodiment of the microscope. In the alternative embodiment of the microscope, the pump laser beam 21 is directed onto the second polarization filter 32. The p-polarized pump laser beam 21 can then be modulated with the aid of the modulator 34. The first minor 26 directs the possibly modulated p-polarized pump laser beam 21 via a dichroic beam splitter 36 onto the scanning unit 38.

Starting out from the light source 20, the Stokes laser beam 31 hits the second mirror 33 and the third mirror 35 which reflect the Stokes laser beam 31 towards the delay stage 30. The delayed Stokes laser beam 31 then passes through the first polarization filter 24 that p-polarizes the Stokes laser beam 31. The p-polarized Stokes laser beam 31 then passes through the circular polarization filter 28 that circularly polarizes the Stokes laser beam 31. The dichroic beam splitter 36 combines the two laser beams 21, 31 so that these hit the scanning unit 38 preferably collinearly. The combined laser beams 21, 31 pass through the scanning unit 38 and are directed via the scan lens 40, the tube lens 42, the beam splitter 44 and the objective 46 onto the sample 48.

The detection light beams emanating from the sample 48 pass in forward direction via the condenser 50 and in reverse direction via the beam splitter 44 to the wavelength-selective elements 52, 58 and the detectors 56, 76, 78. The first wavelength-selective element 52 and the elements arranged downstream thereof such as the third polarization filter 54 and the first detector 56 as well as the second wavelength-selective element 58 correspond to the elements of the first embodiment identified with the same reference signs.

In contrast to the first embodiment, however, the radiation of the second wavelength range of the detection light beam is deflected to a sixth polarization filter 62 that s-polarizes the radiation of the second wavelength range and is then deflected to a fourth detector 76 that detects the Raman-induced Kerr effect. The fourth detector 76 preferably comprises a photomultiplier tube which is sensitive in the near infrared. In addition, the portion of the detection light that is not deflected by the first and the second wavelength-selective element 52, 58, in particular detection light of the third wavelength range, is directed, in contrast to the first embodiment, via a seventh polarization filter 64 that p-polarizes this portion of the detection light onto a fifth detector 78 that is at least sensitive in the third wavelength range. The fifth detector 78 comprises, for example, a large-surface photodiode with lock-in-detection for the demodulation and thus detects the SRG signal.

During operation of the microscope according to the second embodiment, the Stokes laser beam 31 with the fixed wavelength of 1064 nm is circularly polarized, and the pump laser beam 21 can be modulated. In a first step, for detecting fast-running processes in the sample 48, the pump laser beam 21 is not modulated, and with the aid of the first wavelength-selective element 52 radiation of the first wavelength range of the detection light beam is p-polarized and directed onto the first detector 56. Preferably at the same time, radiation of the second wavelength range of the detection light beam is s-polarized with the aid of the sixth polarization filter 62 and directed onto the fourth detector 76, the fourth detector 76 being sensitive at least in the second wavelength range and detecting the RIKES signal at wavelengths of the pump laser radiation.

In a second step, the pump laser beam 21 is modulated with the aid of the modulator 34. Radiation of the third wavelength range of the detection light beam is p-polarized and directed onto the fifth detector 78 that is at least sensitive in the third wavelength range. An output signal of the fifth detector 78 is then demodulated for obtaining the measurement signal, in particular the SRG signal.

In both embodiments, the first wavelength-selective element 52 is preferably selected dependent on the pump laser radiation such that it allows the wavelengths of the pump laser radiation and higher wavelengths to pass through and that it reflects the wavelengths of the CARS or CSRS emission. In both embodiments, the second wavelength-selective element 58 is preferably selected dependent on the pump laser radiation such that it allows higher wavelengths than those of the pump laser radiation to pass through, in particular those of the Stokes laser radiation, and that it reflects the wavelengths of the pump laser radiation.

Each of the two embodiments of the invention allows to detect three different nonlinear Raman effects, wherein two of the Raman effects, namely CARS and RIKES, can be detected simultaneously. In the first embodiment, in addition the SRL signal can be detected, and in the second embodiment in addition the SRG signal can be detected. The pump laser beam 21 and the Stokes laser beam 31 are characterized by their wavelength. The first detector 56 is a CARS detector. The second detector 70 is a pump detector for SRL detection. The third detector 74 is a Stokes detector for RIKES detection. The fourth detector 76 is a pump detector for RIKES detection. The fifth detector 78 is a Stokes detector for SRG detection. The first to fifth detectors 56, 70, 74, 76, 78 can also be referred to as detector units.

Depending on the embodiment, either the pump laser beam 21 is circularly polarized and the Stokes laser beam 31 can be modulated or the Stokes laser beam 31 is circularly polarized and the pump laser beam 21 can be modulated. In this connection, the laser beam that is circularly polarized is referred to as first illumination light beam, and the laser beam that can be modulated is referred to as second illumination light beam.

The invention is not restricted to the embodiments as specified. For example, in both embodiments the detection light beams can be detected exclusively in forward or in reverse direction. Preferably, the RIKES and the CARS signal are detected simultaneously. Alternatively, also the SRS signal can be detected simultaneously with the two other signals or one of the two other signals, then the advantage of fast imaging being lost. Alternatively, also the RIKES and the SRS signal or the CARS and the SRS signal can be detected simultaneously or all three signals can be detected one after the other or all three can be detected simultaneously. In the alternative to the OPO 22, the wavelength of the first laser beam 16 can also be changed in other known ways. In the alternative to CARS, in both embodiments also CSRS can be detected, then the first wavelength-selective element 52 being a short-pass dichroic beam splitter that reflects detection light with wavelengths of the CSRS emission and allows detection light of shorter wavelengths, in particular those of the pump laser radiation and those of the Stokes laser radiation to pass through. Further, also the wavelength of the pump laser radiation can be fixedly predetermined, and the wavelength of the Stokes laser radiation can be variable.

LIST OF REFERENCE SIGNS 16 first laser beam
18 second laser beam
20 light source
21 pump laser beam
22 OPO
24 first polarization filter
25 arrow p-polarized
26 first mirror
27 arrow circularly polarized
28 circular polarization filter
30 delay stage
31 Stokes laser beam
32 second polarization filter
33 second mirror
34 modulator
31 third mirror
36 dichroic beam splitter
38 scanning unit
40 scan lens
42 tube lens
44 beam splitter
46 objective
48 sample
50 condenser
52 first wavelength-selective element
53 point s-polarized
54 third polarization filter
56 first detector
58 second wavelength-selective element
60 fourth polarization filter
62 sixth polarization filter
64 seventh polarization filter
70 second detector
72 fifth polarization filter
74 third detector
76 fourth detector
78 fifth detector

The invention claimed is:

1. An apparatus for the microscopic examination of an object, with an illumination system that generates a first illumination light beam and a second illumination light beam,
   a first polarization filter (28) that circularly polarizes the first illumination light beam,
   a second polarization filter (32) that p-polarizes the second illumination light beam,
   a modulator (34) for modulating the polarized second illumination light beam,
   an excitation optical system that directs the two illumination light beams onto an object,
   a detection optical system that directs detection light beams emanating from the object onto at least two detector units,
   a first detector unit detecting a first nonlinear Raman effect and
   a second detector unit detecting a second nonlinear Raman effect.

2. The apparatus according to claim 1, with a third detector unit that detects a third nonlinear Raman effect.

3. The apparatus according to claim 1, in which each time two of the three detector units simultaneously detect the respective nonlinear Raman effect.

4. The apparatus according to claim 1, the components of which are arranged such that the detection light beams emitted in forward direction with respect to the illumination light beams and/or the detection light beams emitted in reverse direction are detected.

5. An apparatus for the microscopic examination of an object, with an illumination system that generates a first illumination light beam and a second illumination light beam,
   a first polarization filter (28) that circularly polarizes the first illumination light beam,
   a second polarization filter (32) that p-polarizes the second illumination light beam,
   a modulator (34) for modulating the polarized second illumination light beam,
   an excitation optical system that directs the two illumination light beams onto an object,
   a detection optical system that directs detection light beams emanating from the object onto at least two detector units,
   a first detector unit detecting a first nonlinear Raman effect and
   a second detector unit detecting a second nonlinear Raman effect,
   in which the first illumination light beam is a pump laser beam (21) and in which the second illumination light beam is a Stokes laser beam (31),
   with a first wavelength-selective element (52) that directs a first wavelength range of the detection light beam, in which wavelengths of a Stokes emission or anti-Stokes emission lie, via a third polarization filter (54) that p-polarizes the light of the first wavelength range onto a first detector (56) that is sensitive in the first wavelength range,
   a second wavelength-selective element (58) that separates a second wavelength range of the detection light beam, in which wavelengths of the pump laser beam (21) lie, from a third wavelength range, in which wavelengths of the Stokes laser beam (31) lie, and directs it onto a second detector (70) that is sensitive in the second wavelength range,
   a fourth polarization filter (60) that p-polarizes the light of the second wavelength range before it is incident on the second detector (70),
   a demodulator for demodulating the output signal of the second detector (70),
   and with a fifth polarization filter (72) that s-polarizes the light of the third wavelength range that is directed onto a third detector (74) that is sensitive in the third wavelength range.

6. An apparatus for the microscopic examination of an object, with an illumination system that generates a first illumination light beam and a second illumination light beam,
   a first polarization filter (28) that circularly polarizes the first illumination light beam,
   a second polarization filter (32) that p-polarizes the second illumination light beam,
   a modulator (34) for modulating the polarized second illumination light beam,
   an excitation optical system that directs the two illumination light beams onto an object,
   a detection optical system that directs detection light beams emanating from the object onto at least two detector units,
   a first detector unit detecting a first nonlinear Raman effect and
   a second detector unit detecting a second nonlinear Raman effect, in which the first illumination light beam is a Stokes laser beam (31) and in which the second illumination light beam is a pump laser beam (21), with a first wavelength-selective element (52) that directs a first wavelength range of the detection light beam, in which a Stokes emission or anti-Stokes emission lies, via a third polarization filter (54) that p-polarizes the light of the first wavelength range onto a first detector (56) that is sensitive in the first wavelength range, a second wavelength-selective element (58) that separates a second wavelength range of the detection light beam, in which the wavelengths of the pump laser beam (21) lie, from a third wavelength range, in which wavelengths of the Stokes laser beam (31) lie, and directs it onto a fourth detector (76) that is sensitive in the third wavelength range, a sixth polarization filter (62) that s-polarizes the light of the second wavelength range before it is incident on the fourth detector (76), a seventh polarization filter (64) that p-polarizes the light of the third wavelength range directed onto a fifth detector (78) that is sensitive in the third wavelength range, and with a demodulator for demodulating the output signal of the fifth detector (78).

7. A method for examining an object with a microscope, in which a first illumination light beam is generated, the first illumination light beam is circularly polarized, a second illumination light beam is generated, the second illumination light beam is p-polarized, the two polarized illumination light beams (21, 31) are directed onto the object via an excitation optical system, and in which detection light beams emanating from the object are directed onto at least two detector units via a detection optical system, wherein, when the second illumination light beam is not modulated, a first nonlinear Raman effect is detected with a first detector unit, and a second nonlinear Raman effect is detected with a second detector unit.

8. The method according to claim 7, in which the first and the second nonlinear Raman effect are detected simultaneously.

9. The method according to claim 7, in which, when the second illumination light beam is modulated, a third nonlinear Raman effect is detected with a third detector unit.

10. The method according to claim 7, in which the detection beams, starting out from the object, are detected in forward direction and/or in reverse direction with respect to the illumination beams.

11. A method for examining an object with a microscope, in which a first illumination light beam is generated, the first illumination light beam is circularly polarized, a second illumination light beam is generated, the second illumination light beam is p-polarized, the two polarized illumination light beams (21, 31) are directed onto the object via an excitation optical system, and in which detection light beams emanating from the object are directed onto at least two detector units via a detection optical system, wherein, when the second illumination light beam is not modulated, a first nonlinear Raman effect is detected with a first detector unit, and a second nonlinear Raman effect is detected with a second detector unit, in which the first illumination light beam is a pump laser beam (21) and in which the second illumination light beam is a Stokes laser beam (31), and in which, when the Stokes laser beam (31) is not modulated, radiation of a first wavelength range of the detection light beam, in which wavelengths of the Stokes emission or anti-Stokes emission emanating from the sample (48) lie, is p-polarized and directed onto a first detector (56) that is sensitive in the first wavelength range, and radiation of a third wavelength range of the detection light beam, in which wavelengths of the Stokes laser beam (31) lie, is s-polarized and directed onto a third detector (74) that is sensitive in the third wavelength range.

12. The method according to claim 11, in which, when the Stokes laser beam (31) is modulated, radiation of the second wavelength range of the detection light beam is p-polarized and directed onto a second detector (70) that is sensitive in the second wavelength range, an output signal of the second detector (70) is demodulated.

13. A method for examining an object with a microscope, in which a first illumination light beam is generated, the first illumination light beam is circularly polarized, a second illumination light beam is generated, the second illumination light beam is p-polarized, the two polarized illumination light beams (21, 31) are directed onto the object via an excitation optical system, and in which detection light beams emanating from the object are directed onto at least two detector units via a detection optical system, wherein, when the second illumination light beam is not modulated, a first nonlinear Raman effect is detected with a first detector unit, and a second nonlinear Raman effect is detected with a second detector unit, in which the first illumination light beam is a Stokes laser beam (31) and in which the second illumination light beam is a pump laser beam (21), and in which, when the pump laser beam (21) is not modulated, radiation of a first wavelength range of the detection light beam, in which wavelengths of the Stokes emission or anti-Stokes emission emanating from the sample lie, is p-polarized and directed onto a first detector (56) that is sensitive in the first wavelength range, and in which radiation of a second wavelength range of the detection light beam, in which wavelengths of the pump laser beam (31) lie, is s-polarized and directed onto a fourth detector (76) that is sensitive in the second wavelength range.

14. The method according to claim 13, and in which, when the pump laser beam (21) is modulated, radiation of the third wavelength range of the detection light beam is p-polarized and directed onto a fifth detector (78) that is sensitive in the third wavelength range, an output signal of the fifth detector (78) is demodulated.

* * * * *